United States Patent [19]

Mende

[11] Patent Number: 5,024,530

[45] Date of Patent: Jun. 18, 1991

[54] MULTICHANNEL TELECENTRIC FILTERED IMAGER

[75] Inventor: Stephen B. Mende, Los Altos, Calif.

[73] Assignee: Lockheed Missiles & Space Company, Inc., Sunnyvale, Calif.

[21] Appl. No.: 457,079

[22] Filed: Dec. 26, 1989

[51] Int. Cl.$^5$ .................. G01J 3/46; G01N 21/25; G02B 27/12

[52] U.S. Cl. .................. 356/402; 356/419; 350/170

[58] Field of Search .......... 356/328, 346, 244, 351, 356/407, 445, 326, 402, 406, 418, 419; 354/94, 103, 110, 118; 350/96.15, 162.2, 169, 170; 250/461.2, 332; 358/49, 225, 216

[56] References Cited

U.S. PATENT DOCUMENTS

| | | | |
|---|---|---|---|
| 4,146,332 | 3/1979 | Moore | 356/326 |
| 4,609,286 | 9/1986 | Sage, Jr. | 250/461.2 |
| 4,768,853 | 3/1988 | Bhagavatula | 350/96.15 |

OTHER PUBLICATIONS

Instrument for the Monochromatic Observation of all Sky Auroral Images, Mende et al, Applied Optics, Jun. 11, pp. 1691–1700.
A Large Aperture–High–Resolution Fabry–Perot, Spect. for Airglow Studies, Bower et al., 1980, Institute of Physics, pp. 562–567.
Polarization Fourier Spectrometer for Astronomy, A't-learn et al, Applied Optics, May 1974, vol. 13, pp. 1147–1156.
Double Grating Prisms, Nelles, Optik, Aug. 1984, pp. 152–154.
Spectrophotometry of Faint Light Sources; Eather, Applied Optics, Feb. 1969, pp. 227–242.

Primary Examiner—F. L. Evans
Assistant Examiner—K. P. Hantis
Attorney, Agent, or Firm—John J. Morrissey

[57] ABSTRACT

Optical radiation generated by an auroral event is gathered by a fish-eye optical objective (12, 21, 22) and focussed by a telecentric lens (23) to a focal region where a two-passband filter (24) is located. The filter (24) passes two narrow bands of optical radiation, each band of which is centered on a specified wavelength. Rays in the two specified wavelengths are passed by a condenser lens (25) and a collimator lens (26) through an aperture stop in which a blocking filter (27) is located. The blocking filter (27) comprises two side-by-side half-size filters, each of which transmits a corresponding one and suppresses the other of the two specified wavelengths. A prism (28) diffracts rays each of the specified wavelengths by a different amount so that separated images in the two specified wavelengths are formed. A reimaging lens (29) relays the separate images to correspondingly different portions of a detector (30).

16 Claims, 3 Drawing Sheets

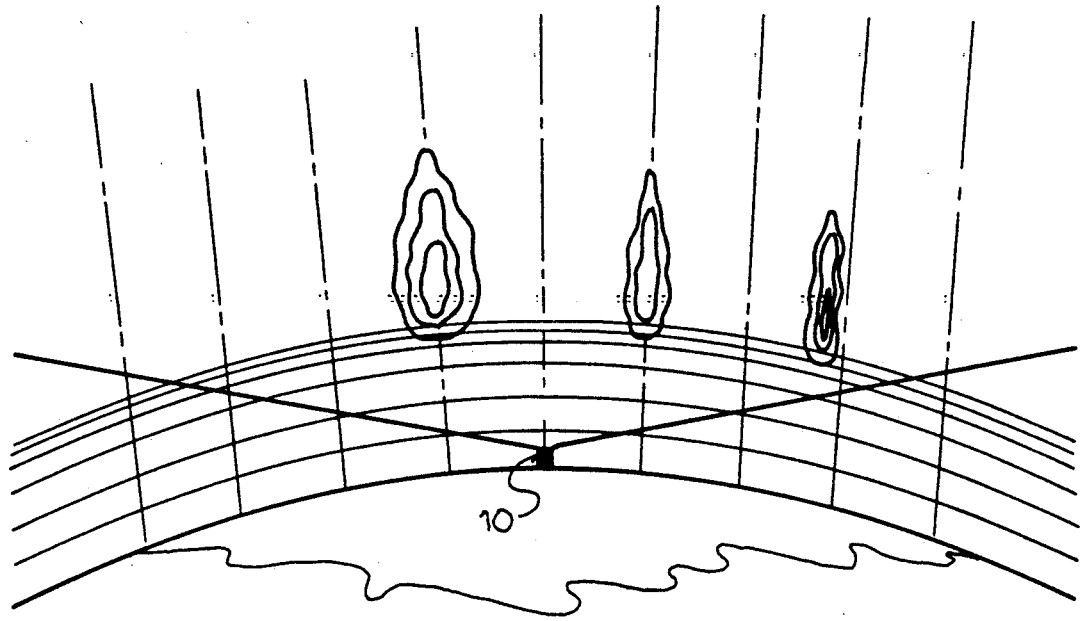
FIG_1
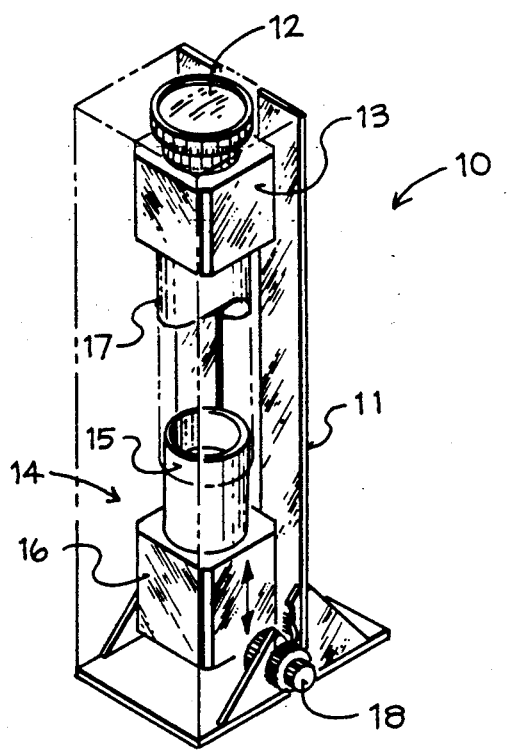
FIG_2

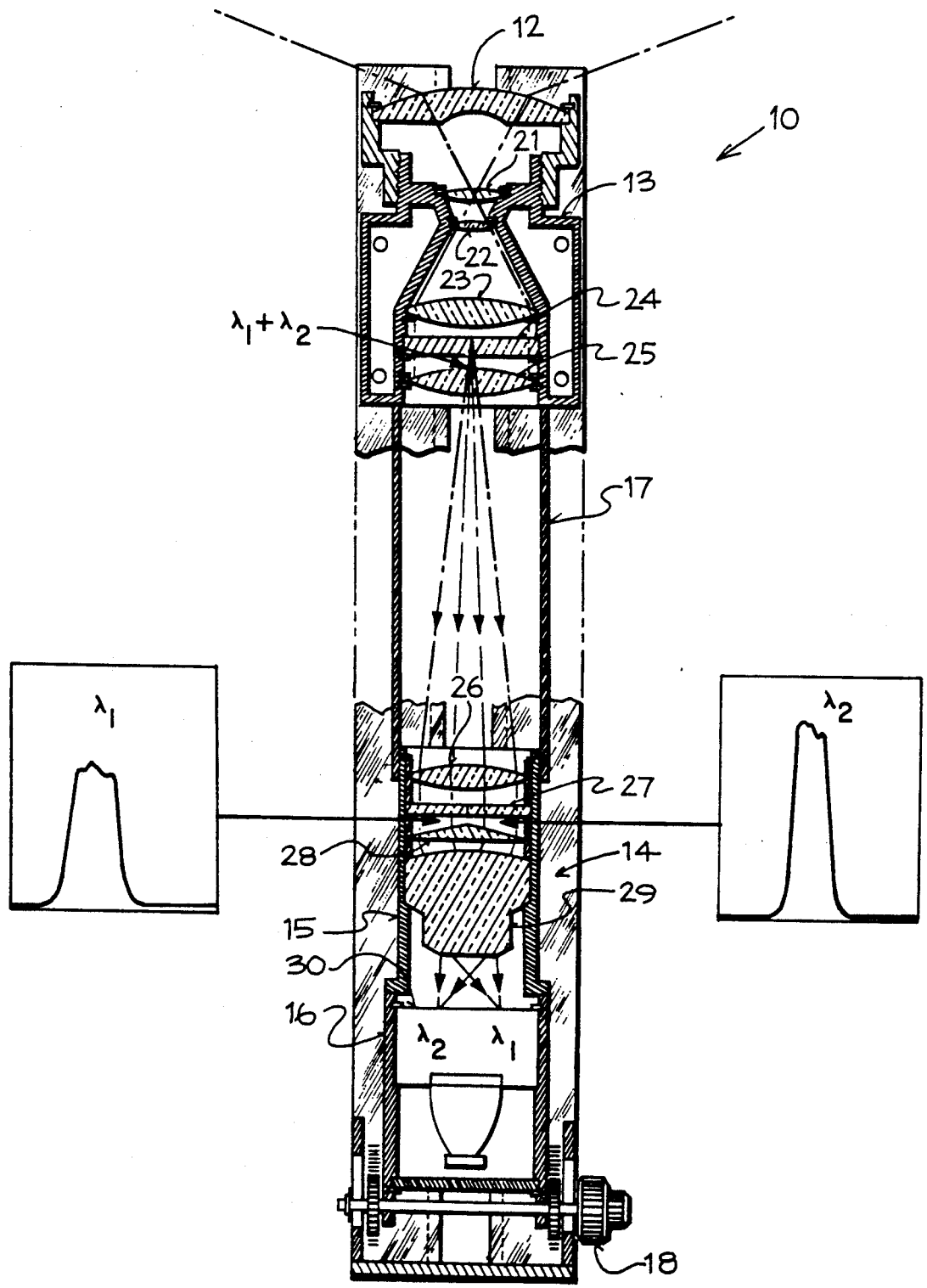
FIG_3

FIG_4
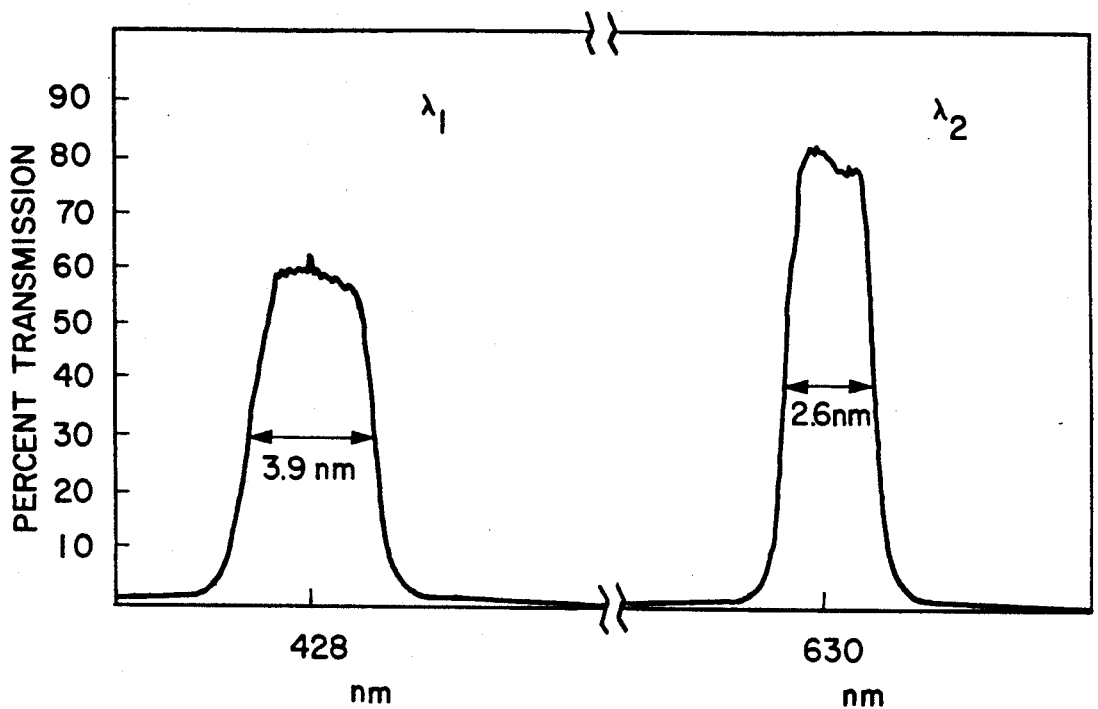
FIG_5
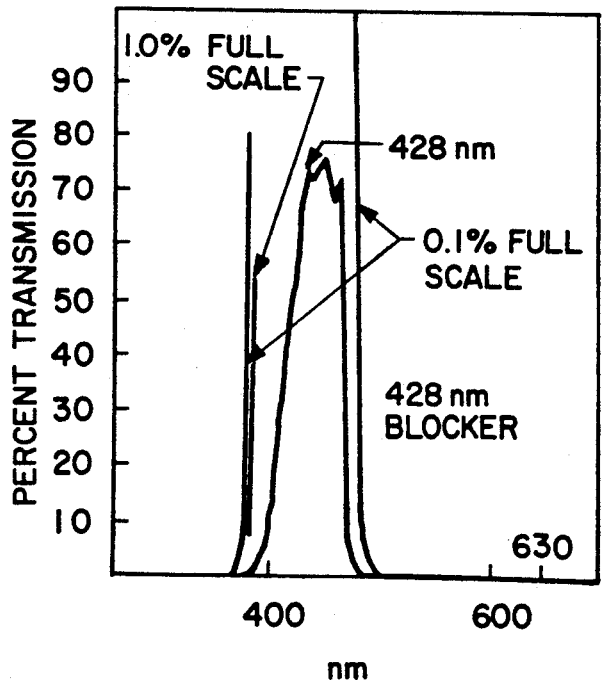
FIG_6
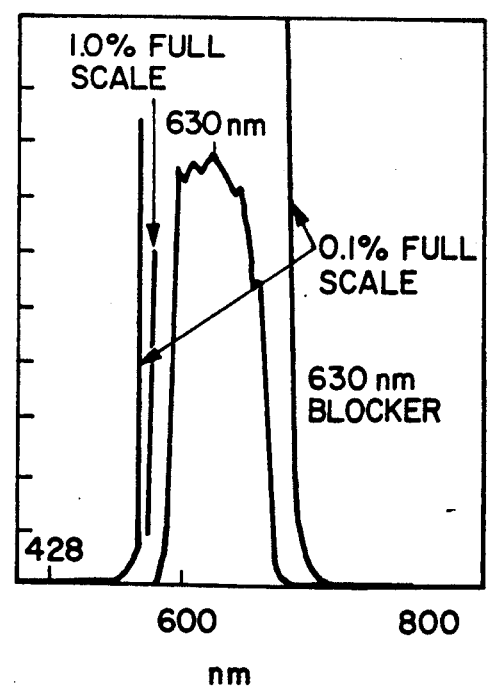

MULTICHANNEL TELECENTRIC FILTERED IMAGER

TECHNICAL FIELD

This invention relates generally to multichannel optical imaging devices, and more particularly to a multichannel telecentric filtered optical imaging device for observing events in the earth's atmosphere that generate optical radiation (e.g., the aurora borealis and the aurora australis).

BACKGROUND OF THE INVENTION

Optical imaging techniques used in the prior art for observing atmospheric events that generate optical radiation in different wavelength bands were generally unable to produce images of a particular event in two or more wavelengths simultaneously. A typical technique of the prior art for observing such atmospheric events involved the use of filter wheels and time-sequencing filters as described in, e.g., and article by S. B. Mende et al. entitled "Instrument for the Monochromatic Observation of All Sky Auroral Images", *Applied Optics*, Vol. 16, No. 6, (June 1977), pages 1691-1700.

In general, filter wheel systems are inconveniently large, and require mechanical actuators and motors that are a significant encumbrance in severe conditions of climate and terrain (e.g., arctic and antarctic conditions) where observations of atmospheric events are of great interest. In addition, in using a filter wheel system for forming images of atmospheric events in different wavelengths, it is also necessary for an image-sequencing system to be coupled to the filter wheel system in order to record annotation data for each image produced. Without such annotation data, there would be no way to correlate a particular image with a particular wavelength. Furthermore, if the atmospheric events being observed involve time-variant phenomena, a comparative analysis of images formed at different times is likely to be plagued with artifacts unrelated to the actual events being observed.

A need had been perceived in the prior art for a technique that enables separate images of events that generate optical radiation (in particular, atmospheric events) to be formed simultaneously in two or more distinct wavelengths.

SUMMARY OF THE INVENTION

It is an object of the present invention to provide a technique for forming separate images simultaneously in different wavelengths of an event that generates optical radiation.

It is a particular object of the present invention to provide a technique for forming separate images simultaneously in different wavelengths of a phenomenon in which optical radiation is generated in different wavelength bands, such as an auroral event occurring in the earth's atmosphere.

In accordance with the present invention, an apparatus is described in which a fish-eye lens is used to gather rays of optical radiation generated by an atmospheric event that is to be observed, and a novel optical system is used to form distinct images of the event simultaneously in different wavelengths side-by-side each other on a detector. The optical system used to form the distinct images of the event in different wavelengths simultaneously comprises an optical objective, a telecentric lens and a reimaging lens, which co-act with a prismatic device and a blocking filter to produce distinct images in each wavelength that are separated from each other on a photodetector.

DESCRIPTION OF THE DRAWING

FIG. 1 is an idealized representation of an atmospheric event that is being imaged in two different wavelengths simultaneously by an imaging apparatus according to the present invention.

FIG. 2 is a perspective view (partially broken away) of an imaging apparatus according to the present invention.

FIG. 3 is a cross-sectional view of the imaging apparatus of FIG. 1.

FIG. 4 is a graphical illustration of percent transmission as a function of wavelength for radiation passed by a filter located adjacent a focal region of an optical objective of the imaging apparatus of FIG. 1, where the passbands of the filter are centered at approximately 428 nm and 630 nm.

FIG. 5 is a graphical illustration of percent transmission as a function of wavelength at full scale, and enlarged to 1.0% and to 0.1% of full scale, for radiation at 428 nm passed by a blocking filter positioned in one half of an aperture located adjacent a prism for separating images in two different wavelengths formed on a detector of the imaging apparatus of FIG. 1.

FIG. 6 is a graphical illustration of percent transmission as a function of wavelength at full scale, and enlarged to 1.0% and to 0.1% of full scale, for radiation at 630 nm passed by a blocking filter positioned in the other half of the aperture located adjacent the prism for separating images in the two different wavelengths formed on the detector of the imaging apparatus of FIG. 1.

BEST MODE OF CARRYING OUT THE INVENTION

FIG. 1 provides an idealized representation of a portion of the Antarctic land mass as viewed from extraterrestrial space, and a surrounding portion of the earth's atmosphere in the vicinity of the South Pole. Straight lines extending from the curved surface of the earth outwardly into space represent flux lines of the earth's magnetic field. High-energy electrically charged particles of extraterrestrial origin that come into proximity with the earth interact with the earth's magnetic field, and are thereby drawn into the earth's atmosphere. Energy-transfer interactions occurring between such charged particles and constituent components of the earth's atmosphere generate, inter alia, bursts of visible electromagnetic radiation (often quite spectacular to the observer) that are generally referred to as the aurora australis.

The wavelength of the visible radiation generated in a particular energy-transfer interaction between an energetic charged particle from space and a constituent atom or ion in the earth's atmosphere depends for the most part upon the nature of the atom or ion that is being bombarded by the charged particle. For example, oxygen atoms emit red radiation at 630 nm, and nitrogen molecular ions emit bluish violet radiation in the 420 nm to 430 mn wavelength band, when bombarded by energetic charged particles. Simultaneous measurements of the relative intensities of radiation in specified optical wavelength bands generated during an auroral event, and a comparison of such measurements with "reference" measurements, can provide an indication of changes in the number flux and in the energy of the charged particles, and in certain cases can also provide an indication of the relative densities of particular species of atoms and ions in the atmosphere at the altitude of the auroral event. Several particular energy-transfer interactions contributing to an auroral event in the earth's atmosphere are indicated in FIG. 1 by clusters of closed-line shapes extending generally longitudinally along flux lines of the earth's magnetic field.

Also shown in FIG. 1 (with a depicted size that is far larger than appropriate for the geographical scale of the illustration) is an imaging apparatus 10 according to the present invention for simultaneously imaging in two different wavelengths an auroral event occurring in the overhead sky. The imaging apparatus 10 is characterized as an "all-sky camera", and has a wide-angle (i.e., greater than 160°) fish-eye type of optical objective for gathering optical radiation from a major portion of the overhead sky. The field of view of the fish-eye optical objective is indicated in vertical cross section in FIG. 1 by solid straight lines extending outward from the top of the imaging apparatus 10.

A particular embodiment of the imaging apparatus 10 of the present invention, which has been installed at South Pole Station, Antarctica, is illustrated in partially broken-away perspective view in FIG. 2. The imaging apparatus 10 is encased in a housing 11 of generally square transverse cross section, which stands approximately three feet high and is approximately eight inches by eight inches in cross-sectional area. A lens element 12 at the top of the housing 11 receives rays in all wavelengths of optical radiation generated by auroral events occurring within its field of view. Rays passed by the lens element 12 enter a compartment 13 that is immovably stationed within the housing 11. Mounted inside the compartment 13 are additional lens elements that coact with the lens element 12 to form a fish-eye optical objective. Also mounted inside the compartment 13 are a telecentric lens, a two-passband optical filter and a condenser lens, as described in detail hereinafter.

Rays leaving the stationary compartment 13 enter a movable compartment 14, which comprises a circularly cylindrical structure 15 and a structure 16 of square transverse cross section coaxially attached to each other. Mounted inside the structure 15 are a collimator lens, a blocking filter, a prism and a reimaging lens, as described in detail hereinafter. Mounted inside the structure 16 is a photodetector, viz., an image-intensified charge coupled device (CCD), as also described hereinafter. A tubular sleeve 17 extends from the stationary compartment 13 to a position in sliding engagement overlapping an end portion of the circularly cylindrical structure 15 to provide a light-tight enclosure within which rays leaving the stationary compartment 13 pass to the movable compartment 14. A gearing mechanism (operated by means of, e.g., a knurled knob 18) enables the movable compartment 14 to be moved axially with respect to the stationary compartment 13 for fine focal adjustment.

In FIG. 3, the imaging apparatus 10 is illustrated in longitudinal cross section. Rays of optical radiation passed by the lens element 12 enter a doublet consisting of lens elements 21 and 22, which coact with the lens element 12 to form the fish-eye optical objective. The optical objective forms an image in a focal region. A telecentric lens 23 is disposed coaxially between the objective lens element 22 and the focal region; and a two-passband filter 24 is positioned adjacent (i.e., generally in the immediate vicinity of) the focal region. A condenser lens 25 is positioned along the optic axis after the focal region.

As shown in FIG. 3, the objective lens elements 21 and 22, the telecentric lens 23, the two-passband filter 24 and the condenser lens 25 are all mounted in a conventional manner coaxially with respect to each other within the stationary compartment 13. The telecentric lens 23 coacts with the lens elements 12, 21 and 22 of the optical objective to cause chief rays emerging from an exit pupil of the optical objective to be substantially parallel to the optic axis. The filter 24 preferably comprises a pair of multilayer interference etalons deposited on a single substrate. The filter 24 permits radiation in two specified narrow wavelength bands to pass, and ideally suppresses all radiation outside the two specified wavelength bands. In any event, the blocking filter mounted in the structure 15 (as mentioned above and as described more thoroughly hereinafter) effectively stops any radiation that might be passed by the filter 24 outside the specified wavelengths bands. The condenser lens 25 is used to ensure that substantially all the radiation passed by the filter 24 enters the movable compartment 14.

In the particular embodiment of the invention illustrated in the drawing, the two specified wavelength bands passed by the filter 24 comprise a band centered at about 428 nm with a bandwidth of about 3.9 nm, and a band centered at about 630 nm with a bandwidth of about 2.6 nm. FIG. 4 shows a curve in which percent transmission is plotted as a function of wavelength for the filter 24. The two peaks in the curve shown in FIG. 4 indicate the two specified passbands centered at 428 nm (designated as $\lambda_1$) and 630 nm (designated as $\lambda_2$), respectively. The peak representing the passband centered at 428 nm indicates a transmission of about 60% at $\lambda_1$ with a width-at-half-height (i.e., a bandwidth) of 3.9 nm; and the peak representing the passband centered at 630 nm indicates a transmission of about 80% at $\lambda_2$ with a width-at-half-height (i.e., a bandwidth) of 2.6 nm.

As illustrated in FIG. 3, rays of optical radiation in the two passbands transmitted by the filter 24, which is located adjacent the focal region, are directed by the condenser lens 25 into the movable compartment 14. A collimator lens 26 mounted in the circularly cylindrical structure 15 of the movable compartment 14 ensures that rays in both wavelength passbands from all points on the image formed in the focal region are made substantially parallel to each other. Parallel rays from the collimator lens 26 then enter a wavelength-discriminating device, which comprises a blocking filter 27 and a prism 28. The blocking filter 27 consists of two half-size blockers placed side-by-side, one of which transmits radiation only at 428 nm (i.e., $\lambda_1$) and thus suppresses radiation in the 630 nm passband, and the other of which transmits radiation only at 630 nm (i.e., $\lambda_2$) and thus suppresses radiation in the 428 nm passband.

The blocking filter 27 is located in a circular aperture provided in the structure 15 of the movable compartment 14. It is a feature of the imaging apparatus 10 in accordance with the present invention that the optical interference function performed by the filter 24 to define the specified wavelength passbands has been separated from the blocking function performed by the filter 27 to suppress radiation outside the specified wavelength passbands. Separation of these two functions enables the interference filter 24 to be located where the rays transmitted by the optical objective are substantially paraxial, and enables the blocking filter 27 to be located somewhere else where the direction of the rays is inconsequential. The prism 28 is mounted adjacent the blocking filter 27 in the structure 15, and is configured (i.e., has an appropriate apex angle) so that rays incident thereon in the two different wavelengths $\lambda_1$ and $\lambda_2$ transmitted by the blocking filter 27 are deflected by different amounts whereby separate images in the two different wavelengths are relayed to correspondingly different portions of the detector.

A left-hand marginal illustration in FIG. 3 with an arrow pointing to a region between the left half of the blocking filter 27 and the left half of the prism 28 indicates the radiation transmitted in $\lambda_1$ only; and a right-hand marginal illustration in FIG. 3 with an arrow pointing to a region between the right half of the blocking filter 27 and the right half of the prism 28 indicates the radiation transmitted in $\lambda_2$ only. In FIG. 5, a graphical illustration is provided of percent transmission as a function of wavelength for the left half of the blocking filter 27 that transmits the $\lambda_1$ radiation. Also indicated in FIG. 5 is percent transmission as a function of wavelength at full scale, and at 1.0% and 0.1% of full scale (i.e., when the ordinate scale is multiplied by 100 and by 1000, respectively), for radiation at $\lambda_1$ passed by the left half of the blocking filter 27 to illustrate the effectiveness of the suppression at $\lambda_2$. In FIG. 6, a graphical illustration is provided of percent transmission as a function of wavelength for the right half of the blocking filter 27 that transmits the $\lambda_2$ radiation. Also indicated in FIG. 6 is percent transmission as a function of wavelength at full scale, and at 1.0% and 0.1% of full scale, for radiation at $\lambda_2$ passed by the right half of the blocking filter 27 to illustrate the effectiveness of the suppression at $\lambda_1$.

The prism 28 and the blocking filter 27 are positioned with respect to each other so that rays in the wavelength band centered on $\lambda_1$ are incident upon the left half of the prism 28, and rays in the wavelength band centered on $\lambda_2$ are incident upon the right half of the prism 28. The left half of the prism 28 deflects the rays centered on $\lambda_1$ by an amount different than the amount by which the right half of the prism 28 deflects the rays centered on $\lambda_2$. A conventional reimaging lens 29, which in a particular embodiment might comprise several constituent transmissive elements not shown in the drawing, relays separate images in each of the two wavelengths $\lambda_1$ and $\lambda_2$ to a detector 30. The apex angle of the prism 28 is specified so that the separate images in each of the two wavelengths $\lambda_1$ and $\lambda_2$ formed on the detector 30 are displaced with respect to each other so as not to overlap each other on the detector 30. In the preferred embodiment of the invention, the detector 30 is an intensified charge coupled device (CCD).

The present invention has been described above in terms of a particular embodiment designed for a particular application. However, other embodiments of the invention for other applications would be apparent to practitioners skilled in the art upon perusal of the foregoing description and the accompanying drawing. The description and drawing presented herein are merely illustrative of the invention, which is more broadly defined by the following claims and their equivalents.

I claim:

1. An apparatus for enabling a distant object that emits rays of optical radiation in a plurality of wavelength bands to be separately imaged upon a detector in a plurality of distinct wavelengths simultaneously, each distinct wavelength being within a corresponding one of said wavelength bands, said apparatus comprising:
   a) a lens system comprising an objective lens means, a telecentric lens means and a reimaging lens means, all disposed coaxially with respect to each other along an optic axis; said objective lens means causing rays of optical radiation emitted by said object to form an image at a focal region; said telecentric lens means being positioned between said objective lens means and said focal region to cause chief rays emerging from a central portion of an exit pupil of said objective lens means to be substantially parallel to said optic axis; said reimaging lens means relaying said image onto said detector;
   b) filter means disposed adjacent said focal region where said chief rays are substantially parallel to said optic axis, said filter means passing rays of said optical radiation within said wavelength bands to said reimaging lens means, said filter means suppressing optical radiation in wavelengths outside said wavelength bands; and
   c) wavelength-discriminating means disposed between said filter means and said detector for causing said image of said object formed at said focal region and relayed onto said detector to appear simultaneously as a plurality of distinct images on said detector, said distinct images being spatially separated from each other on corresponding portions of said detector, each of said distinct images being formed by rays of a corresponding one of said plurality of distinct wavelengths.

2. The apparatus of claim 1 wherein said wavelength-discriminating means comprises:
   (a) a blocking filter comprising means for passing to each portion of said detector substantially only rays in said corresponding one of said plurality of distinct wavelengths; and
   (b) a prismatic device disposed adjacent said blocking filter, said prismatic device having an apex angle such that said rays passed by said blocking filter are defected so that said distinct images appearing on said corresponding portions of said detector are separated from each other.

3. The apparatus of claim 1 wherein said objective lens means functions as a fish-eye lens for gathering optical radiation.

4. The apparatus of claim 1 wherein said filter means disposed adjacent said focal region comprises a plurality of multilayer interference etalons.

5. The apparatus of claim 1 further comprising a condenser lens disposed coaxially between said filter means and said wavelength-discriminating means.

6. The apparatus of claim 5 further comprising a collimator lens disposed coaxially between said condenser lens and said wavelength-discriminating means.

7. The apparatus of claim 2 further comprising means defining an aperture adjacent said prismatic device, said blocking filter being disposed in said aperture.

8. The apparatus of claim 1 in which said detector comprises a charge coupled device.

9. An apparatus for observing an event that generates rays of optical radiation in a plurality of wavelength bands in a specified region of the earth's atmosphere, said apparatus comprising:
   (a) a lens system comprising an objective lens means, a telecentric lens means and a reimaging lens means, all disposed coaxially with respect to each other along an optic axis; said objective lens means causing rays of optical radiation generated by said event to form an image at a focal region; said telecentric lens means being positioned between said objective lens means and said focal region to cause chief rays emerging from a central portion of an exit pupil of said objective lens means to be substantially parallel to said optic axis; said reimaging lens means relaying said image onto a detector;

(b) filter means disposed adjacent said focal region where said chief rays are substantially parallel to said optic axis, said filter means passing rays of said optical radiation within said wavelength bands to said reimaging lens means, said filter means suppressing optical radiation in wavelengths outside said wavelength bands; and (c) wavelength-discriminating means disposed between said filter means and said detector for causing said image formed at said focal region and relayed onto said detector to appear simultaneously as a plurality of distinct images on said detector, said distinct images being spatially separated from each other on corresponding portions of said detector, each of said distinct images being formed by rays of a corresponding one of said plurality of distinct wavelengths.

10. The apparatus of claim 9 wherein said wavelength-discriminating means comprises:

(a) a blocking filter comprising means for passing to each portion of said detector substantially only rays in said corresponding one of said plurality of distinct wavelengths; and (b) a prismatic device disposed adjacent said blocking filter, said prismatic device having an apex angle such that said rays passed by said blocking filter are deflected so that said distinct images appearing on said corresponding portions of said detector are separated from each other.

11. The apparatus of claim 9 wherein said objective lens means functions as a fish-eye lens for gathering optical radiation generated by said event.

12. The apparatus of claim 9 wherein said filter means disposed adjacent said focal region comprises a plurality of multilayer interference etalons.

13. The apparatus of claim 9 further comprising a condenser lens disposed coaxially between said filter means and said wavelength-discriminating means.

14. The apparatus of claim 13 further comprising a collimator lens disposed coaxially between said condenser lens and said wavelength-discriminating means.

15. The apparatus of claim 10 further comprising means defining an aperture adjacent said prismatic device, said blocking filter being disposed in said aperture.

16. The apparatus of claim 9 in which said detector comprises a charge coupled device.

* * * * *